US012017082B2

(12) United States Patent
Greene et al.

(10) Patent No.: US 12,017,082 B2
(45) Date of Patent: Jun. 25, 2024

(54) MANUFACTURING IMPLANTABLE TISSUE STIMULATORS

(71) Applicant: Curonix LLC, Pompano Beach, FL (US)

(72) Inventors: Graham Patrick Greene, Miami Beach, FL (US); Benjamin Speck, Pompano Beach, FL (US); Paul Lombard, Coral Springs, FL (US)

(73) Assignee: CURONIX LLC, Pompano Beach, FL (US)

( * ) Notice: Subject to any disclaimer, the term of this patent is extended or adjusted under 35 U.S.C. 154(b) by 688 days.

(21) Appl. No.: 17/097,891

(22) Filed: Nov. 13, 2020

(65) Prior Publication Data

US 2021/0170184 A1 Jun. 10, 2021

Related U.S. Application Data

(60) Provisional application No. 62/934,849, filed on Nov. 13, 2019.

(51) Int. Cl.
*H01L 21/60* (2006.01)
*A61N 1/372* (2006.01)
(Continued)

(52) U.S. Cl.
CPC ....... *A61N 1/3756* (2013.01); *A61N 1/37223* (2013.01); *H01L 21/56* (2013.01);
(Continued)

(58) Field of Classification Search
CPC ..... A61N 1/37223; H01L 21/56; H01L 21/64; B29C 45/14336; B29L 2031/753; Y10T 29/4913; Y10T 29/49146
See application file for complete search history.

(56) References Cited

U.S. PATENT DOCUMENTS 7,856,707 B2   12/2010  Cole
8,494,641 B2*  7/2013   Boling ................. A61N 1/0558
                                                          607/46
(Continued)

FOREIGN PATENT DOCUMENTS

WO   WO 2012/138782   10/2012
WO   WO 2013/019757   2/2013
(Continued)

OTHER PUBLICATIONS

International Preliminary Report on Patentability in International Appln. No. PCT/US2020/060578, dated May 27, 2022, 7 pages.
(Continued)

*Primary Examiner* — Donghai D Nguyen

(57) ABSTRACT

A method of manufacturing an implantable stimulation device includes providing a circuit board of the implantable stimulation device, the circuit board optionally equipped with circuit components and being electrically connected to an antenna, adhering one or more electrodes to the circuit board, and applying an insulation material to the circuit board such that the insulation material forms a housing that surrounds the circuit board, the optional circuit components and antenna, while leaving the one or more electrodes exposed for stimulating a tissue.

18 Claims, 14 Drawing Sheets

(51) Int. Cl.
  *A61N 1/375*   (2006.01)
  *H01L 21/56*   (2006.01)
  *H01L 21/64*   (2006.01)
  *B29C 45/14*   (2006.01)
  *B29L 31/00*   (2006.01)

(52) U.S. Cl.
  CPC .............. *H01L 21/60* (2021.08); *H01L 21/64* (2013.01); *B29C 45/14336* (2013.01); *B29L 2031/753* (2013.01); *H01L 2021/60007* (2013.01)

(56) References Cited

U.S. PATENT DOCUMENTS

| | | | |
|---|---|---|---|
| 8,897,894 | B1 | 11/2014 | Orinski |
| 9,220,897 | B2 | 12/2015 | Perryman et al. |
| 9,248,276 | B2 | 2/2016 | Pianca et al. |
| 9,789,314 | B2 | 10/2017 | Perryman et al. |
| 9,808,613 | B2 * | 11/2017 | McDonald ............ A61N 1/057 |
| 10,238,874 | B2 | 3/2019 | Perryman et al. |
| 10,245,436 | B2 | 4/2019 | Perryman et al. |
| 10,485,980 | B2 * | 11/2019 | Yeh ................... A61N 1/36125 |
| 11,439,832 | B2 | 9/2022 | Perryman et al. |
| 2006/0161204 | A1 | 6/2006 | Colvin et al. |
| 2007/0219551 | A1 | 9/2007 | Honour et al. |
| 2010/0010565 | A1 | 1/2010 | Lichtenstein et al. |
| 2011/0130816 | A1 | 6/2011 | Howard et al. |
| 2014/0031837 | A1 | 1/2014 | Perryman et al. |
| 2015/0366508 | A1 | 12/2015 | Chou et al. |
| 2016/0023003 | A1 | 1/2016 | Perryman et al. |
| 2016/0101287 | A1 | 4/2016 | Perryman et al. |
| 2016/0184597 | A1 | 6/2016 | Andresen et al. |
| 2017/0143959 | A1 | 5/2017 | Boling et al. |
| 2017/0165476 | A1 | 6/2017 | Greenberg et al. |
| 2018/0008821 | A1 | 1/2018 | Gonzalez et al. |
| 2018/0008828 | A1 | 1/2018 | Perryman et al. |
| 2018/0169406 | A1 | 6/2018 | Shah et al. |
| 2018/0289971 | A1 | 10/2018 | Yeh et al. |
| 2019/0143124 | A1 | 5/2019 | Perryman et al. |
| 2019/0247660 | A1 | 8/2019 | Perryman et al. |
| 2019/0282297 | A1 | 9/2019 | Schultz |
| 2020/0206521 | A1 | 7/2020 | Chen |
| 2020/0215333 | A1 | 7/2020 | Perryman et al. |
| 2023/0056224 | A1 | 2/2023 | Perryman et al. |

FOREIGN PATENT DOCUMENTS

| | | |
|---|---|---|
| WO | WO 2013/025632 | 2/2013 |
| WO | WO 2013/040549 | 3/2013 |
| WO | WO 2012/103519 | 3/2014 |

OTHER PUBLICATIONS

PCT International Search Report and Written Opinion in International Apln. No. PCT/US2020/060578, dated Jan. 11, 2021, 8 pages.

* cited by examiner

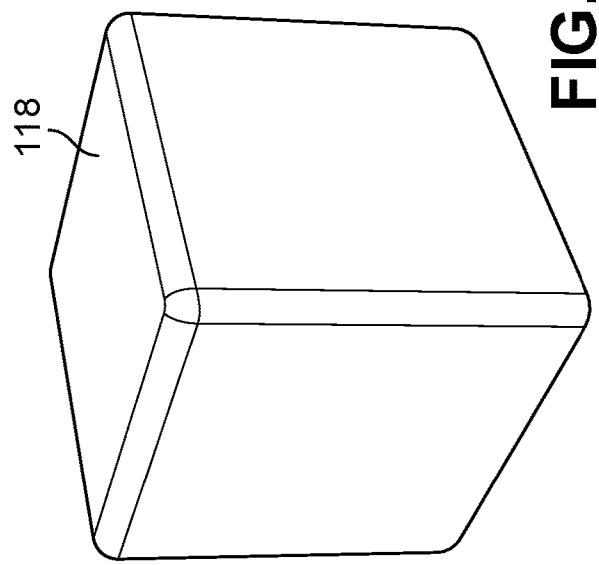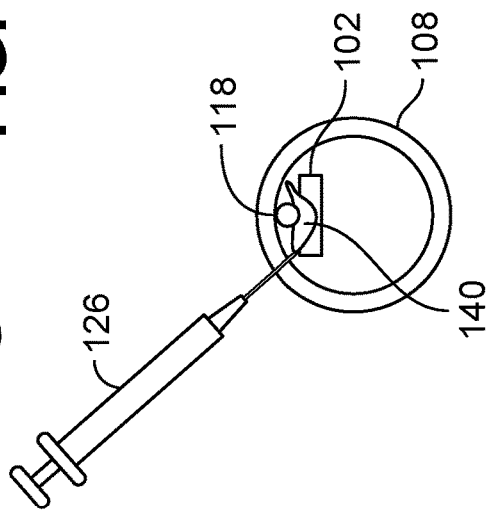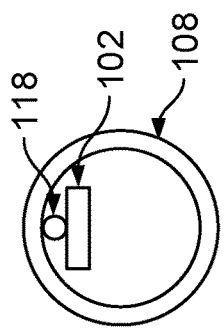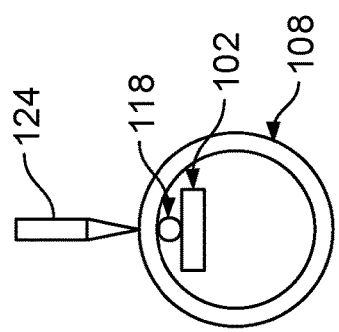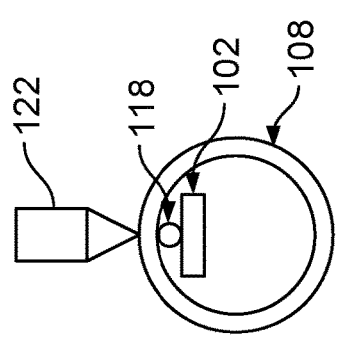

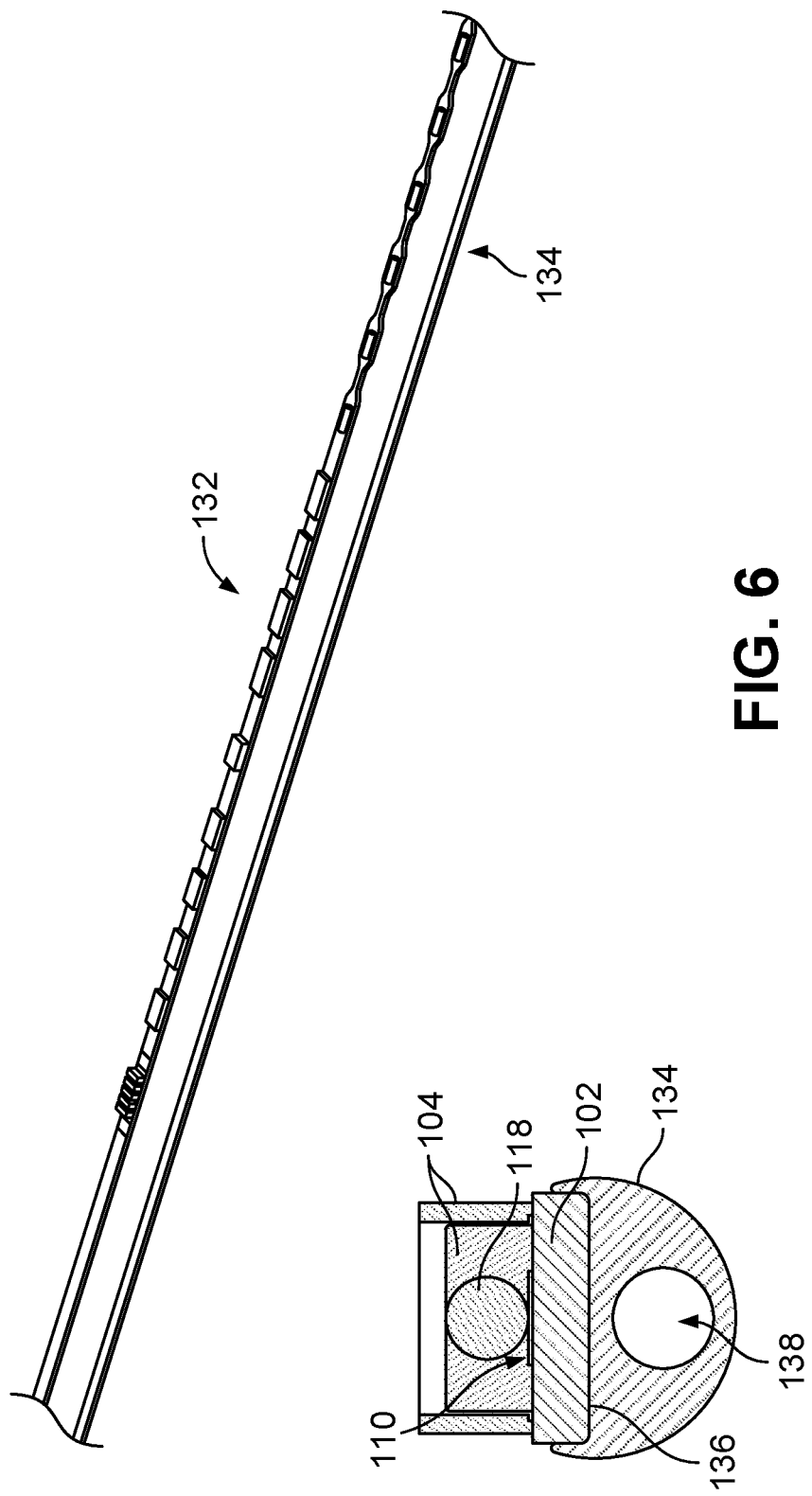

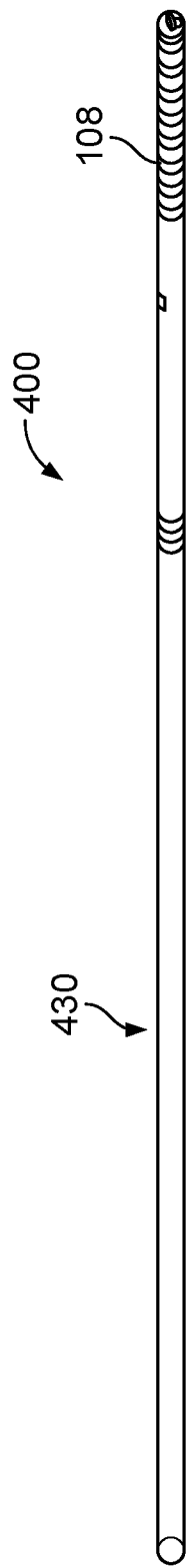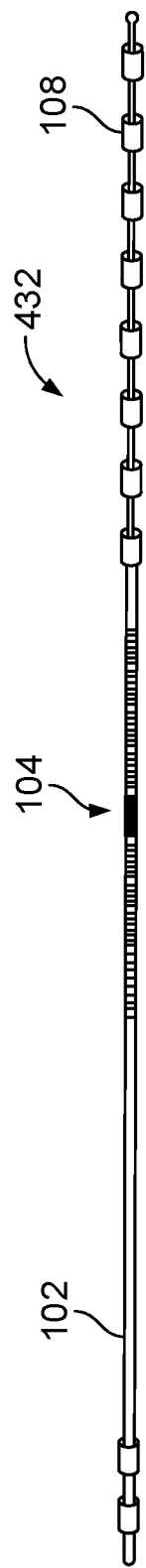
FIG. 12
FIG. 13

MANUFACTURING IMPLANTABLE TISSUE STIMULATORS

CROSS REFERENCE TO RELATED APPLICATION

This application claims priority to U.S. Provisional Patent Application No. 62/934,849, filed on Nov. 13, 2019. The entire content of this application is incorporated herein by reference.

TECHNICAL FIELD

This disclosure relates to manufacturing implantable tissue stimulators using various overmolding techniques.

BACKGROUND

Modulation of tissue within the body by electrical stimulation has become an important type of therapy for treating chronic, disabling conditions, such as chronic pain, problems of movement initiation and control, involuntary movements, dystonia, urinary and fecal incontinence, sexual difficulties, vascular insufficiency, and heart arrhythmia. For example, an external antenna can be used to send electrical energy to electrodes on an implanted tissue stimulator that can pass pulsatile electrical currents of controllable frequency, pulse width, and amplitudes to a tissue.

SUMMARY

In general, this disclosure relates to methods of manufacturing implantable tissue stimulators, such as methods that incorporate injection molding or dip coating techniques.

In one aspect, a method of manufacturing an implantable stimulation device includes providing a circuit board of the implantable stimulation device, the circuit board being equipped with circuit components and an antenna, adhering one or more electrodes to the circuit board, and applying an insulation material to the circuit board such that the insulation material forms a housing that surrounds the circuit board, the circuit components, and the antenna, while leaving the one or more electrodes exposed for stimulating a tissue.

Embodiments may include one or more of the following features.

In some embodiments, the method further includes attaching one or more joints to the circuit board and, after attaching the one or more joints, adhering the one or more electrodes to the circuit board respectively at the one or more joints.

In some embodiments, the method further includes attaching the one or more joints to the circuit board automatically by soldering, laser welding, or applying a conductive epoxy.

In some embodiments, the method further includes forming the one or more joints such that each of the one or more joints has a cube-like shape.

In some embodiments, the method further includes manufacturing the implantable stimulation device without any cables.

In some embodiments, the method further includes positioning the circuit board atop a support component, the support component defining a through opening sized to allow passage of a surgical tool, and covering the circuit board with a protective component, the protective component defining a channel that accommodates the circuit components on the circuit board.

In some embodiments, the method further includes alternately placing one or more spacers and the one or more electrodes over an assembly of the support component, the circuit board, and the protective component, placing an extended housing component over the assembly, and adhering the one or more spacers, the one or more electrodes, and the extended housing component to the circuit board.

In some embodiments, the one or more spacers and the extended housing component includes carbothane or other flexible polymer.

In some embodiments, the assembly is a first assembly, wherein the first assembly, the one or more spacers, the one or more electrodes, and the extended housing component together form a second assembly, and wherein the method further includes surrounding the second assembly with a heat shrink tube.

In some embodiments, the method further includes flowing the flexible polymer around the second assembly in a reflow tower and, after flowing the flexible polymer, removing the heat shrink tube from the second assembly.

In some embodiments, the insulation material of the implantable stimulation device is provided by at least one of the extended housing component and the one or more spacers.

In some embodiments, the method further includes securing the second assembly, equipped with the heat shrink tube, to a clamp of the reflow tower, and translating a heating element shuttle of the reflow tower along the second assembly to flow the flexible polymer into the second assembly.

In some embodiments, the method further includes placing an assembly of the circuit board, equipped with the circuit components, the antenna, and the one or more electrodes, within an injection mold.

In some embodiments, the method further includes filling the injection mold with the insulation material to form a housing of the implantable stimulation device.

In some embodiments, the injection mold defines one or more cavities that extend perpendicular to the implantable stimulation device, and the method further includes forming one or more tissue fixation devices respectively at the one or more cavities.

In some embodiments, the insulation material includes liquid silicone rubber.

In some embodiments, the method further includes dip coating an assembly of the circuit board, equipped with the circuit components, the antenna, and the one or more electrodes, to form a housing of the implantable stimulation device.

In some embodiments, the housing includes the insulation material.

In another aspect, an implantable stimulation device includes a circuit board equipped with circuit components, an antenna, and one or more electrodes. The implantable stimulation device further includes a housing formed of an insulation material that surrounds the circuit board, the circuit components, and the antenna, the insulation material leaving the one or more electrodes exposed for stimulating a tissue.

In some embodiments, the implantable stimulation device further includes one or more joints by which the one or more electrodes are adhered to the circuit board, each of the one or more joints having a cube-like shape.

DESCRIPTION OF DRAWINGS

FIG. 4A is a side cross-sectional view of a circuit board of the electronic assembly of FIG. 2 with electrodes attached thereto.

FIG. 4B is a perspective view of a joint of the electronic assembly of FIG. 2.

FIG. 5 illustrates various techniques by which the electrodes of FIG. 4 can be attached to the circuit board of FIG. 4, including laser welding, soldering, and conductive epoxy application.

FIGS. 6-9 illustrate a series of steps involved in manufacturing the tissue stimulator of FIG. 1.

FIG. 12 is a perspective view of a tissue stimulator manufactured in part by dip coating.

FIG. 13 is a subassembly of the tissue stimulator of FIG. 12 that is dipped in a solution to form the tissue stimulator of FIG. 12.

DETAILED DESCRIPTION

Figure 1:
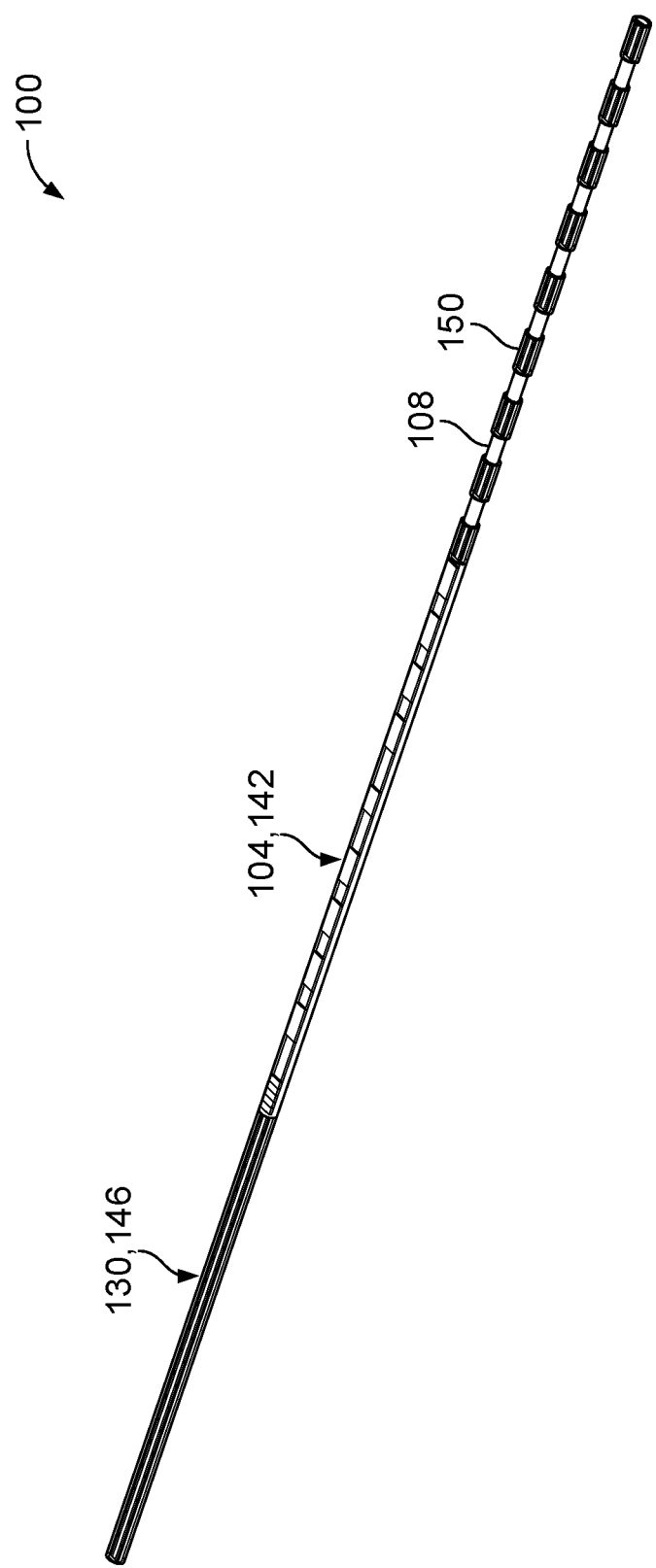
FIG. 1 is a perspective view of a tissue stimulator manufactured in part using an injection molding technique with extrusion components.
Figure 2:
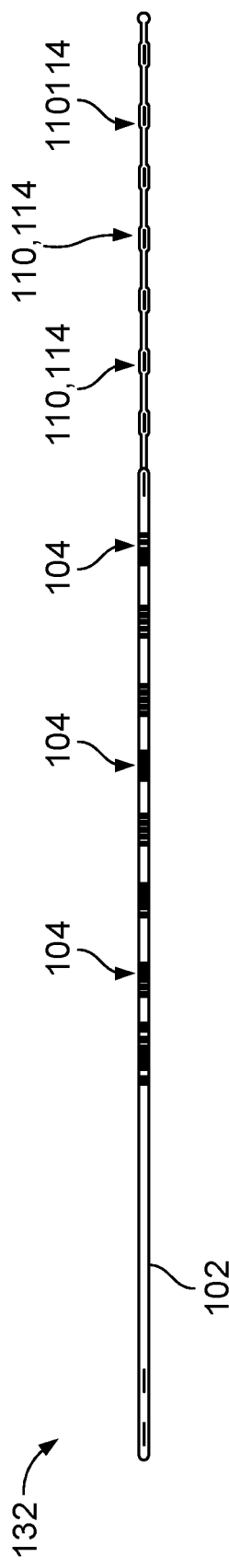
FIG. 2 is a top view of an electronic assembly of the tissue stimulator of FIG. 1.
Figure 3:
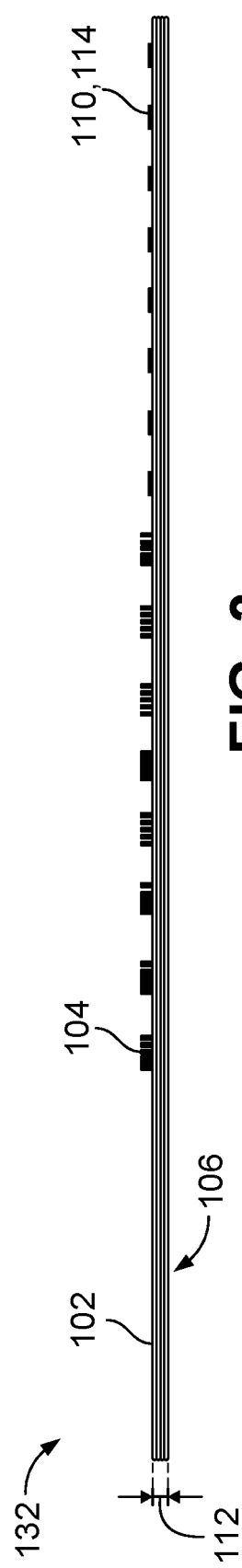
FIG. 3 is a side view of the electronic assembly of FIG. 2.

FIG. 1 illustrates a tissue stimulator 100 designed to be implanted within a patient's body for delivering electrical therapy to tissues within the body. The tissue stimulator 100 has an overmolded exterior design that provides strength and a smooth profile for optimal insertion and performance within the patient. For example, the tissue stimulator 100 includes a housing 130 that is molded (e.g., overmolded or injection molded) of a transparent (e.g., clear), opaque, or translucent material around various internal components of the tissue stimulator 100. Accordingly, the tissue stimulator 100 is a monolithic device for which electronic components are secured to a small, flat substrate and that can be delivered to the body through an introducer needle. Referring to FIGS. 1-3, the tissue stimulator 100 further includes a circuit board 102, various circuit components 104, an antenna 106, and electrodes 108 that are secured to the circuit board 102, as well as spacers 150 that are arranged alternately with the electrodes 108. The tissue stimulator 100 further includes multiple pads 110 at which the electrodes 108 are respectively attached to the one or more circuit boards 102.

In some embodiments, a tissue stimulator that is substantially similar in construction and function to the tissue stimulator 100 may alternatively include more than one of any of the above-mentioned components. For example, in addition to the electrodes 108, the pads 110, and the spacers 150, such a tissue stimulator may include one or more antennas 106, as well as one or more circuit boards 102 that are each provided as one or more small, flat substrates.

Referring still to the example tissue stimulator 100 of FIGS. 1-3, the circuit board 102 is provided as one or more flexible substrates, including multiple layers 112 in which at least one antenna 106 is interposed. The circuit board 102 defines contact sites 114 that locate the pads 110. Each pad 110 typically has a length of about 0.5 mm to about 4 mm, a width of about 0.05 mm to about 0.5 mm, and a thickness of about 0.0125 mm to about 0.5 mm. The circuit board 102 is typically made of a dielectric substrate, such as polyimide. In some embodiments, additional dielectric materials may be applied to the circuit board 102 along certain regions for stiffening.

The circuit components 104 are distributed along the length of the circuit board 102 and may be secured to the circuit board 102 via solder, solder paste, or conductive epoxy. Example circuit components 104 include diodes, capacitors, resistors, semiconductors, and other electromechanical components. The antenna 106 is integrated directly into one of the layers 112 of the circuit board 102 and is designed to receive an input signal carrying electrical energy that can be used by the circuit components 104 and relayed to the electrodes 108 so that the electrodes 108 can apply one or more electrical pulses to adjacent tissue. Arrangement of the antenna 106 along a layer 112 contributes to a compact and simplified structure of the electronic device 100 in that such configuration avoids the need for additional cables or attachment features to communicate the antenna 106 with the circuit components 104. In some embodiments, the tissue stimulator 100 may include additional trace pathways to serialize the circuit components 104 and render the electronic device 100 viewable with standard imaging equipment (e.g., X-ray equipment). For example, the circuit board 102 may include one or more built-in coupling traces that can extend a transmission zone of the tissue stimulator 100. Such coupling traces may or may not be directly connected to the primary circuit components 104 (e.g., as in the case of near field RF coupling). An electronic assembly 132 including a circuit board 102 that is equipped with circuit components 104, an antenna 106, and layers 112 may be manufactured individually or in an array of individual electronic assemblies 132 as part of a mass production process. The electrodes 108 are embodied as generally cylindrical structures that can be secured to the pads 110 at the contact sites 114. The electrodes 108 typically have a length of about 0.5 mm to about 6 mm and an internal diameter of about 0.9 mm to about 1.5 mm. Referring to FIGS. 2-4, the electrodes 108 are attached to the contact sites 114 and around the circuit board 102 at joints 118. The joints 118 provide additional surface area at which the electrodes 108 can be attached to the circuit board 102. The electrodes 108 and the joints 118 are typically made of one or more biocompatible materials (e.g., noble metals or other metals) that have good conductivity characteristics and that therefore result in a good tissue response, such as stainless steel, platinum, platinum-iridium, gallium-nitride, titanium-nitride, iridium-oxide, or other materials. The joints 118 may have cross-sectional shape that is substantially circular (e.g., as shown in FIG. 4A), triangular, square, square-round, rectangular, or similar to any of these shapes. The joints 118 may have a three-dimensional shape that is substantially spherical (e.g., corresponding to the circular cross-sectional shape shown in FIG. 4), substantially cubic or cube-like (e.g., as shown in FIG. 4B), or that is of another shape. A shape of the joints 118 provides an outer surface at which the electrodes 108 can be sufficiently attached to the contact sites 114. Furthermore, the joints 118 can serve as fiducial markers (e.g., radio-opaque markers or other types of visual markers).

In some embodiments, the joints 118 are attached to the circuit board 102 at the contact sites 114 in an automatic manner (e.g., via surface mount techniques that utilize tape and reel machine mechanisms) at a high production rate with reduced labor. In some embodiments, the joints 118 are soldered to the circuit board 102 by hand. The joints 118, embodied as any of the shapes described above, typically have a thickness of about 0.05 mm to about 0.5 mm and typically have a length that is a bit shorter than the respective electrodes 108. The circuit board 102 and the joints 118 are sized, dimensioned, and arranged to promote filing of cavities with insulation material that forms the housing 130 during manufacturing of the tissue stimulator 100, as will be discussed in more detail below.

Referring to FIG. 5, the electrodes 108 may then be attached to the circuit board at the joints 118 using various attachment techniques, such as laser welding, soldering, and conductive epoxy application (e.g., chemical bonding). Such techniques can be carried out automatically using computer controlled processing heads (e.g., laser heads 122, soldering tips 124, and syringes 126 applying epoxy 140) that can be controlled to attach multiple electrodes 108 to the joints 118 on the circuit board 102 in one pass or in multiple passes. In this manner, the electrodes 108 can be attached to the circuit board 102 in a uniform manner within specified tolerances and without cables (e.g., stainless steel wires, braided wires, or other wires) extending along the circuit board 102 and between the electrodes 108 that would otherwise need to be manually assembled with the electrodes 108 and the circuit board 102. In some embodiments, the electrodes 108 may be slid over the circuit board 102 and positioned at the joints 118 as part of the laser welding, soldering, or epoxy techniques discussed above. For example, a microscope with optical tweezers or other specialty tooling and equipment may be used to position the electrodes 108 along the circuit board 102.

As compared to conventional implantable electronic devices for which electrodes are secured to a circuit board via multiple cables, the tissue stimulator 100 is more easily assembled (e.g., automatically and more quickly at a lower cost), more flexible, can withstand more bending forces (e.g., avoiding the problem of cables popping off of electrodes), is more mechanically robust within a moving body, and is therefore less likely to fail mechanically. Additionally, the electrodes 108 may be assembled more uniformly with respect to positional accuracy and mechanical integrity, as compared to electrodes that are manually secured to a circuit board with multiple cables.

In some embodiments, an overall footprint and shape of the tissue stimulator 100 are selected to provide optimized electrical and mechanical performance of the circuit components 104 and the electrodes 108, provide a minimal overall size of the tissue stimulator 100, and provide an anchoring structure that prevents or reduces movement of the tissue stimulator 100 within the body.

FIGS. 6-9 illustrate a series of steps involved in manufacturing the tissue stimulator 100. Referring to FIG. 6, the electronic assembly 132 is placed atop a lower component 134 (e.g., a support component). The lower component 134 is an elongate component that extends a length at least as long as the length of the circuit board 102. The lower component 134 has a generally semi-circular outer cross-sectional shape and defines a flat recessed surface 136 for supporting the circuit board 102. The lower component 134 defines an interior through channel 138 that is sized to allow passage of ancillary surgical equipment, such as a steering stylet, a rigidity stylet, or an implantable receiver, etc. The lower component 134 typically has a length of about 1 cm to about 38 cm or more and a maximum width (e.g., a diameter) of about 0.5 mm to about 2.0 mm. The interior through channel 138 typically has a diameter of about 0.2 mm to about 1.0 mm.

Figure 7:
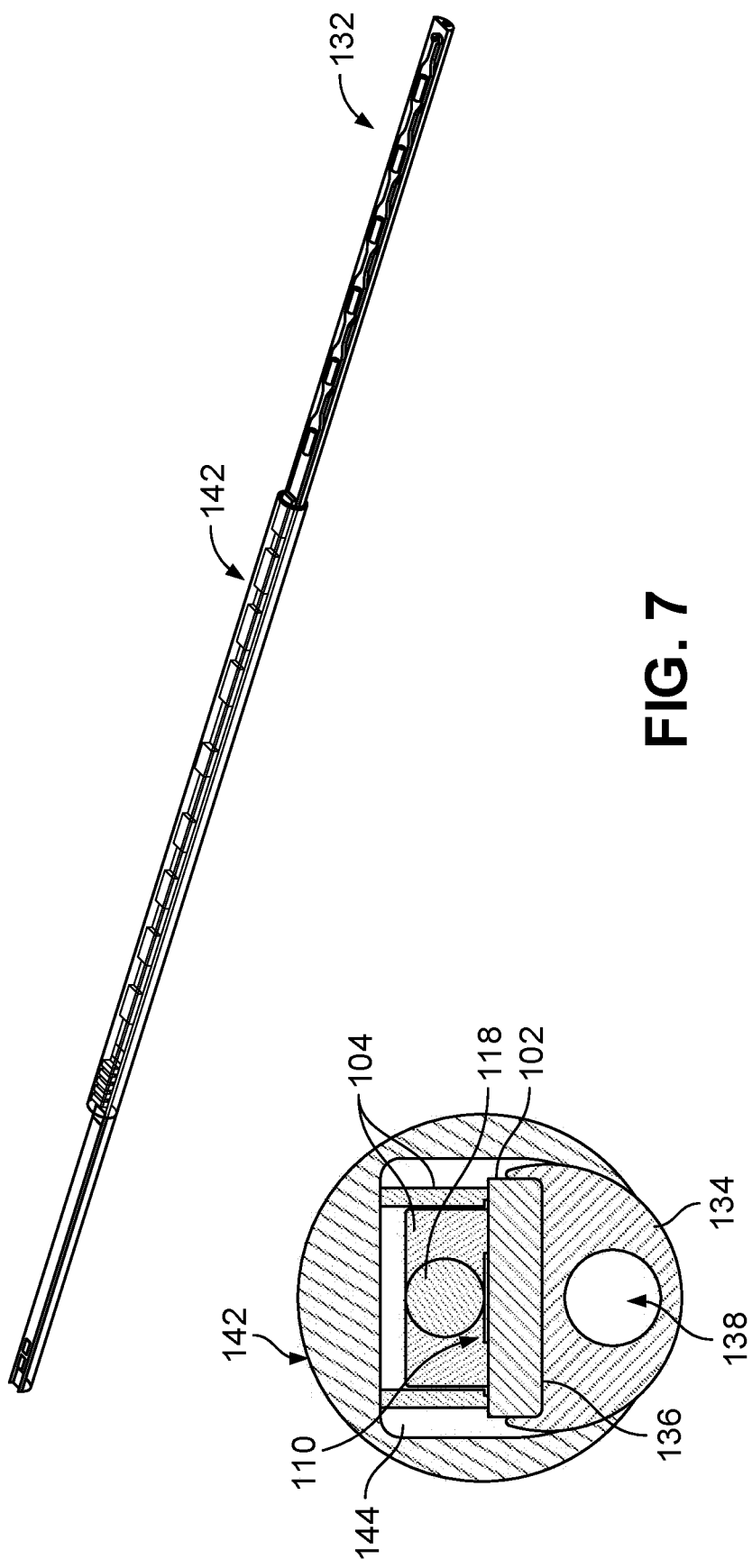

Referring to FIG. 7, an upper component 142 (e.g., a protective component) is subsequently placed atop the electronic assembly 132 (e.g., over the circuit components 104) while the electronic assembly 132 is supported on the lower extrusion component 134. The upper component 142 is an elongate component that extends a length of about 1 cm to about 30 cm or more to protect the circuit components 104. The upper component 142 has a generally circular outer cross-sectional shape and defines a generally rectangular channel 144 that is sized to fit over the circuit components 104 and the width of the lower component 134. Both the lower and upper components 134, 142 are typically made of polyurethane or other flexible polymers such as carbothane, pellethane, silicone, or thermoplastic polyurethane (TPU) and may be formed via extrusion, injection molding or other suitable technique.

In some embodiments, a tissue stimulator that is similar in construction and function to the tissue stimulator 100 may not be formed using the upper component 142 and may instead be formed with a cylindrical tube that has an inner diameter fitting around the outer diameter of the electronic assembly 132.

Figure 8:
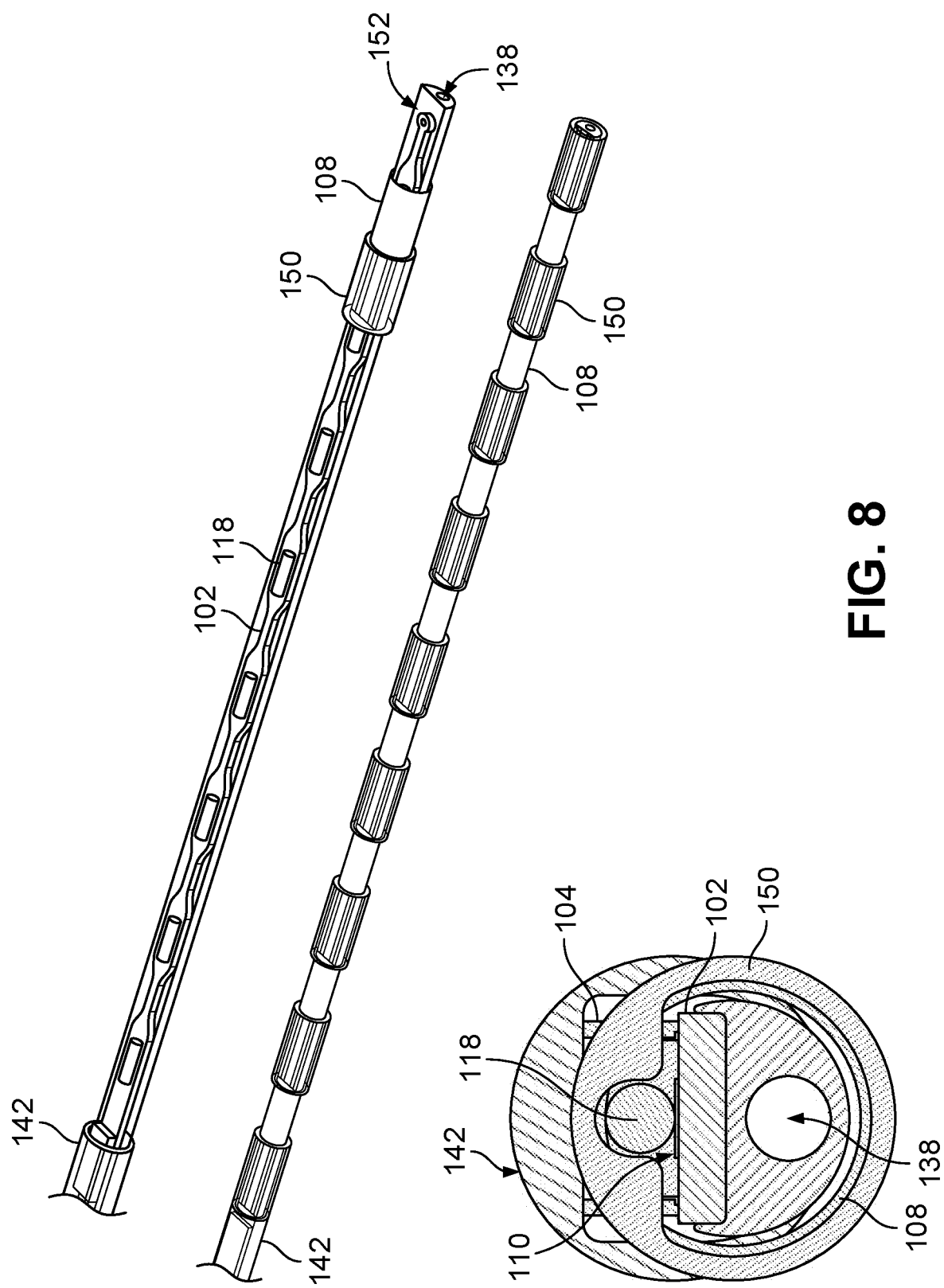

Referring to FIG. 8, the electrodes 108 and the spacers 150 are slid over and positioned along the electronic assembly 132. For example, an electrode 108 may be attached to a joint 118 in an automated manner via any of techniques discussed above with respect to FIG. 5. A spacer 150 then may be slid over and positioned adjacent to the attached electrode 108 in an automated manner. For example, the spacers 150 may be placed on the electronic assembly 132 using an automated fixture that slides the spacers 150 into position and then welds, melds, or melts the spacers 150 in place. The spacers 150 have a generally circular outer cross-sectional shape and an inner cross-sectional shape that is formed to pass over the lower component 134 and the joints 118 attached thereto. The spacers 150 typically have a length of about 0.5 mm to about 6 mm and an internal diameter of about 0.2 mm to about 1.5 mm. The spacers 150 are typically made of materials that can reflow when heat is applied to create a water-tight seal against surrounding components, such as the components of the electronic assembly 132. For example, the spacers 150 may be made of flexible biocompatible polymers, such as polyurethane, pellethane, carbothane, or silicone. Another electrode 108 is positioned against a free end of the spacer 150 and attached to a respective joint 118, and the remaining spacers 150 and electrodes 108 are assembled to the circuit board 102 in a like manner in an alternating arrangement.

Figure 9:
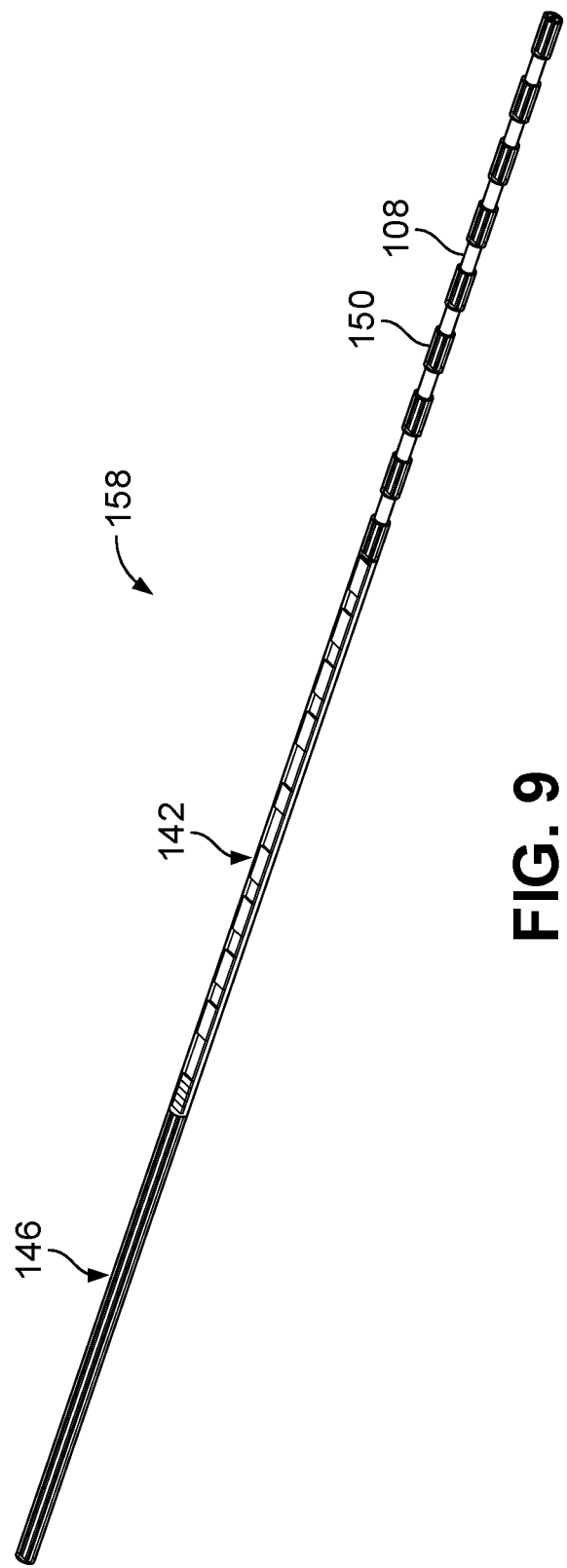

Referring to FIG. 9, an extended housing component 146 is placed (e.g., slid) over an end of the circuit board 102 that is opposite the electrodes 108. The component 146 typically has a length of about 1 mm to about 450 mm and an internal diameter of about 0.2 mm to about 1.5 mm. The component 146 may be made of the same material from which the spacers 150 are made. When all of the spacers 150 and the component 146 are made of the same polymer material, the spacers 150 and the component 146 are fused together molecularly during a heating process to provide the strong, durable bonds. The lower and upper components 134, 142 may also or instead be formed of the same polymer material as spacers 150. Furthermore, components 134 and 142 may be lengthened, making component 146 unnecessary. The assembly 158 as shown in FIG. 9 is then placed in a reflow tower, where a piece of heat shrink tube (not shown) is placed (e.g., automatically placed) around the entire assembly 158. In some implementations, the piece of heat shrink tube is placed around the assembly 158 before the assembly 158 is placed in the reflow tower. Once the entire assembly 158 is reflowed (as described below), the heat shrink tube is cut and peeled off of the assembly 158, revealing the tissue stimulator 100 as illustrated in FIG. 1. Upon completion of the manufacturing process, the interior channel 138 extends nearly the full length of the tissue stimulator 100.

Figure 10A:
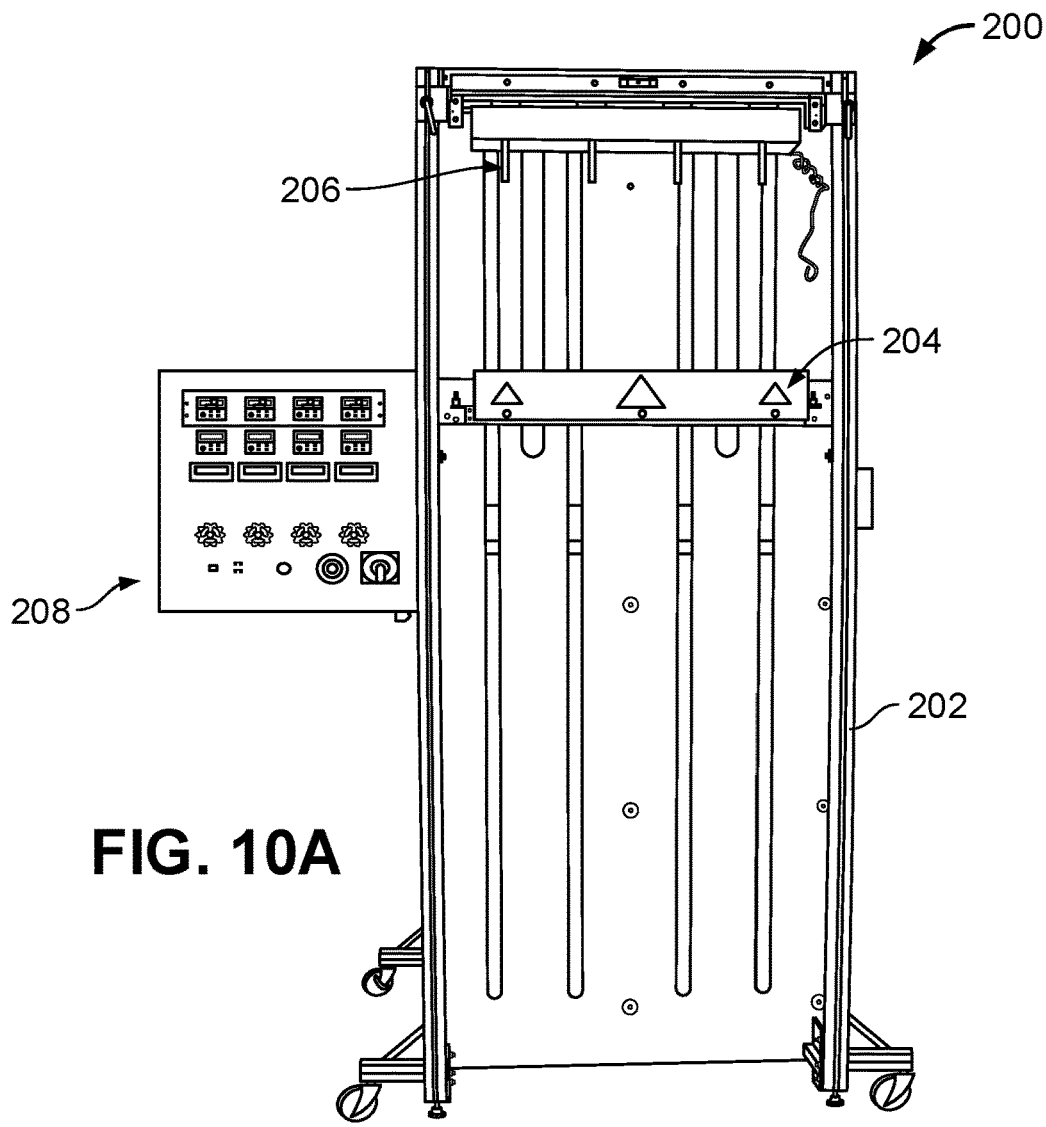
FIG. 10A illustrates a reflow tower that can be used to manufacture the tissue stimulator of FIG. 1.

FIG. 10A illustrates an example reflow tower 200 that can be used to perform the manufacturing step shown in FIG. 9. The reflow tower 200 includes a support frame 202, a heating element shuttle 204 that is translatable vertically along the support frame 202, and multiple (e.g., four) clamps 206 that are designed to grasp components, such as mandrels, tissue stimulators 100, catheters, or other products. The grasped components remain stationary while the heating element shuttle 204 moves along (e.g., around and without touching) the length of the grasped components. The reflow tower 200 also includes a control panel 208 by which several parameters (e.g., speed, timing, and temperature) can be controlled, potentially for each of the grasped components.

Figure 10B:
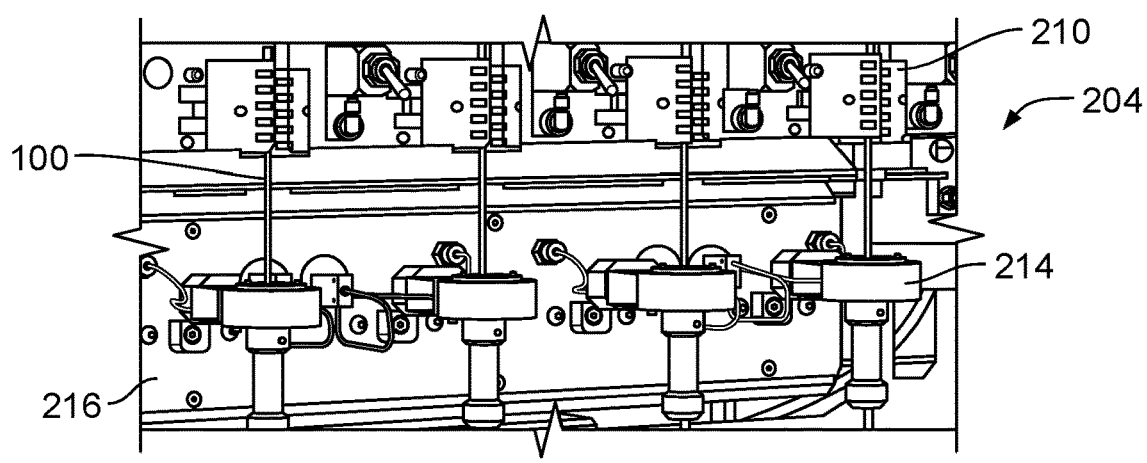
FIG. 10B illustrates an enlarged view of a portion of the reflow tower of FIG. 10A.

FIG. 10B is an enlarged view of the heating element shuttle 204. Shown in FIG. 10B is a plastic stabilizing component 210, a heater band 214, heating support components 216, and the tissue stimulators 100. The tissue stimulators 100 are stationary, and the heating element shuttle 204 moves along the length of the tissue stimulators 100 as governed at the control panel 208.

A coated mandrel (e.g., coated with polytetrafluoroethylene) is placed inside of assemblies 158 that have been wrapped with heat shrink tube and that have been clamped into the reflow tower 200, which may be hanging vertically. When the reflow process is initiated, the precise, temperature-controlled heating element shuttle 204 traverses the length of an assembly 158 to reflow the polymer material, e.g., of the spacers 150 and the component 146, to molecularly join them together, thereby unifying the assembly 158 section by section.

Figure 11A:
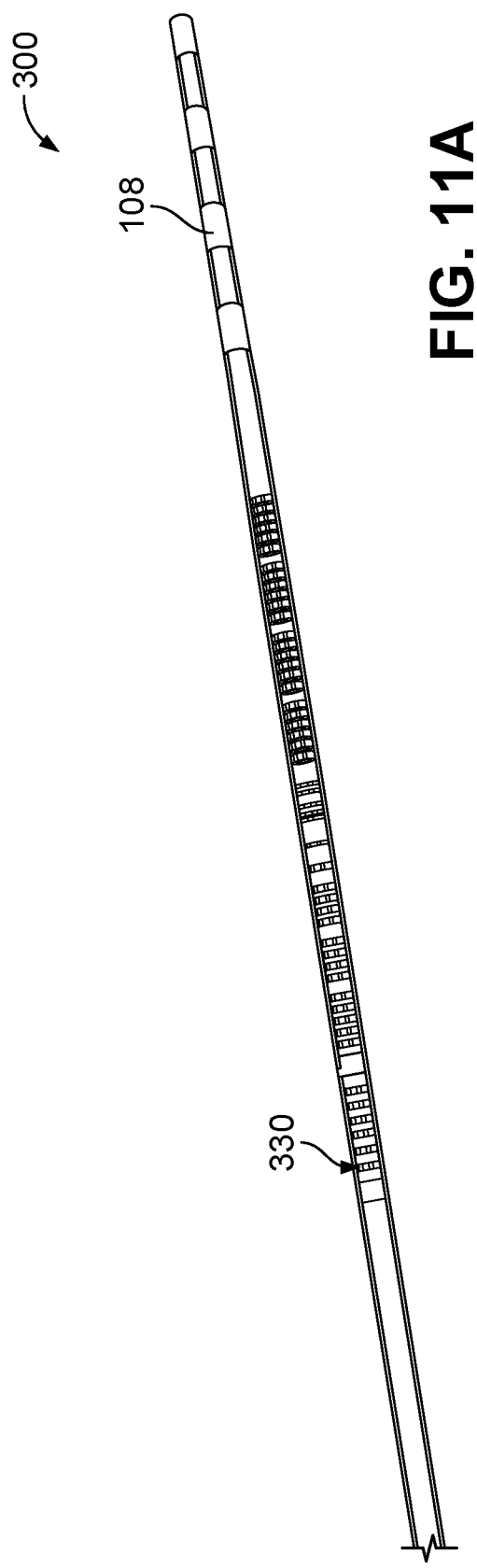
FIG. 11A is a perspective view of a tissue stimulator manufactured in part using an injection molding technique with a silicone material.

In some embodiments, a tissue stimulator that is similar in construction and function to the tissue stimulator 100 may be manufactured via overmolding with a different material, such as silicone. For example, FIG. 11A illustrates such a tissue stimulator 300 that is substantially similar in construction and function to the tissue stimulator 100, except that a housing 330 of the tissue stimulator 300 is formed from a different insulation material, such as liquid silicone rubber. Accordingly, the tissue stimulator 300 further includes a circuit board 102, various circuit components 104, an antenna 106, and electrodes 108 that are secured to the circuit board 102. Spaces between the electrodes 108 are filled during the overmold process with the liquid silicone rubber. Accordingly, the tissue stimulator 300 does not include the spacer components 150. The tissue stimulator 300 also includes multiple pads 110 at which the electrodes 108 are respectively attached to the circuit board 102, as discussed above with respect to the tissue stimulator 100.

In some embodiments, a tissue stimulator that is substantially similar in construction and function to the tissue stimulator 300 may alternatively include more than one of any of the above-mentioned components. For example, in addition to the electrodes 108 and the pads 110, such a tissue stimulator may include one or more antennas 106 and one or more circuit boards 102.

Figure 11B:
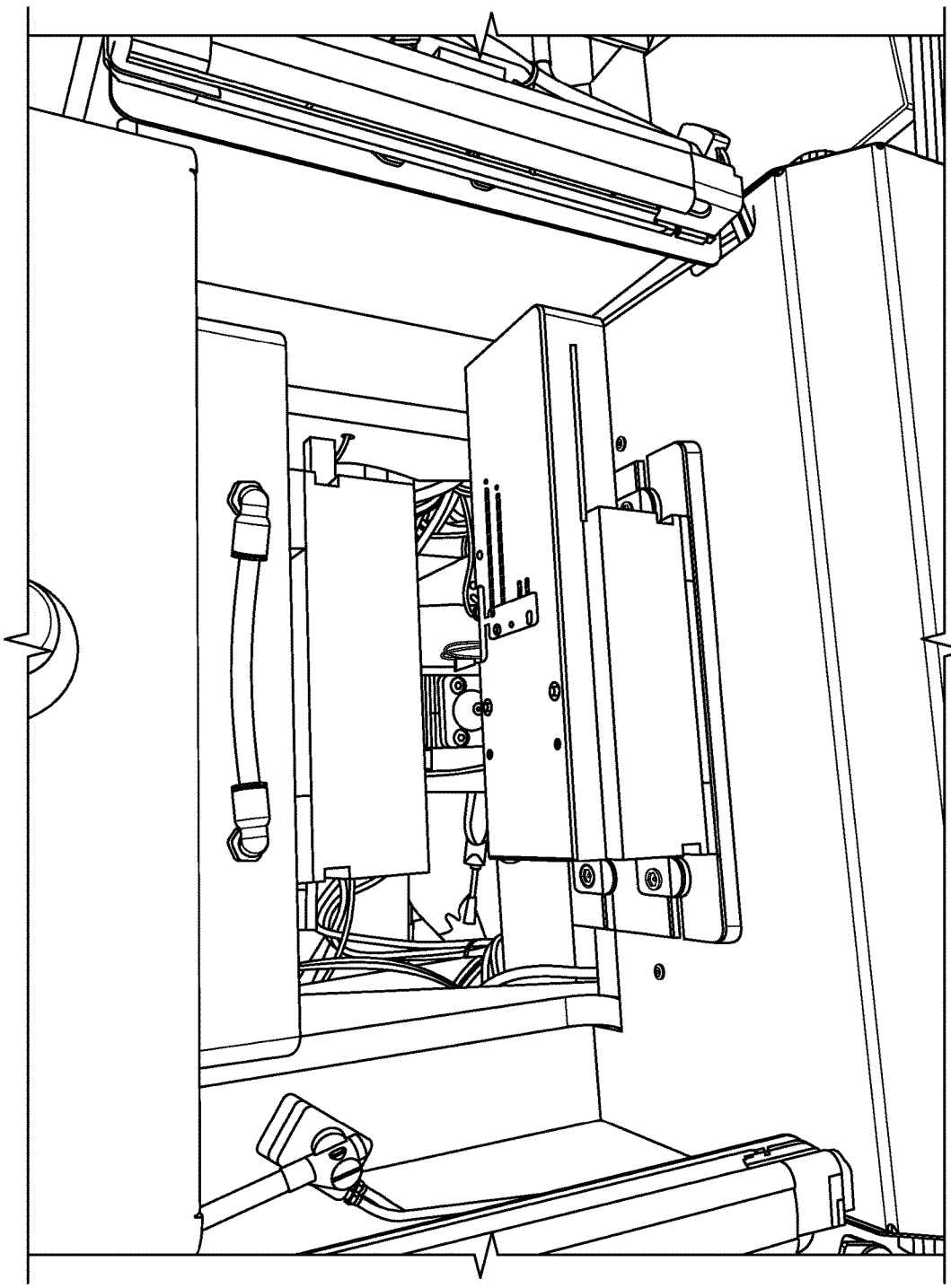
FIG. 11B illustrates an injection mold that can be used to manufacture the tissue stimulator of FIG. 11A.

Referring still to the example tissue stimulator 300, FIG. 11B illustrates an injection mold 350 (e.g., a cavity mold) that can be used to manufacture the tissue stimulator 300. In some embodiments, the tissue stimulator 300 may be manufactured by placing an assembly of the circuit board 102, equipped with the circuit components 104, the antenna 106, and the electrodes 108 inside of the injection mold 350 and fixtured in such a way that the assembly is encased (e.g., entirely encased) in the insulation material to form a cylindrical shape of the housing 330. For example, the insulation material is injection molded under high pressure or low pressure or gravity poured to fill a mold with the assembly in place. The insulation material flows and fills all cavities and curves of the assembly, but does not overflow the electrodes 108, which are intended to contact a patient's tissue. In some embodiments, the mold may have cavities that extend perpendicular to the tissue stimulator 300 to form fixation features (e.g., tines) on the housing 130 that provide a tissue anchoring capability to the tissue stimulator 300.

In some embodiments, a tissue stimulator that is similar in construction and function to the tissue stimulator 100 may be manufactured using a dip coating process. For example, FIG. 12 illustrates such a tissue stimulator 400 that is substantially similar in construction and function to the tissue stimulator 100, except that a housing 430 of the tissue stimulator 400 and spaces between electrodes 108 are formed by dip coating. Accordingly, the tissue stimulator 400 further includes a circuit board 102, various circuit components 104, an antenna 106, electrodes 108 that are secured to the circuit board 102, and multiple pads 110 at which the electrodes 108 are respectively attached to the circuit board 102, as discussed above with respect to the tissue stimulator 100.

For example, an insulation material may be formed by dissolving polyurethane in a solvent to form a liquid solution. Referring to FIG. 13, an assembly 432 that includes the circuit board 102 equipped with the circuit components 104, the antenna 106, and the electrodes 108 is dipped into the liquid solution to coat the assembly 432 with the liquid solution. Iterative dips may be performed to achieve a desired cylindrical shape and diameter of the tissue stimulator 400. For example, dip coating applies the liquid solution layer by layer. After an initial dip, the assembly is air dried for a period of time to evaporate a liquifying chemical component of the liquid solution, and then the process is repeated to iteratively increase a diameter of the assembly.

Figure 14:
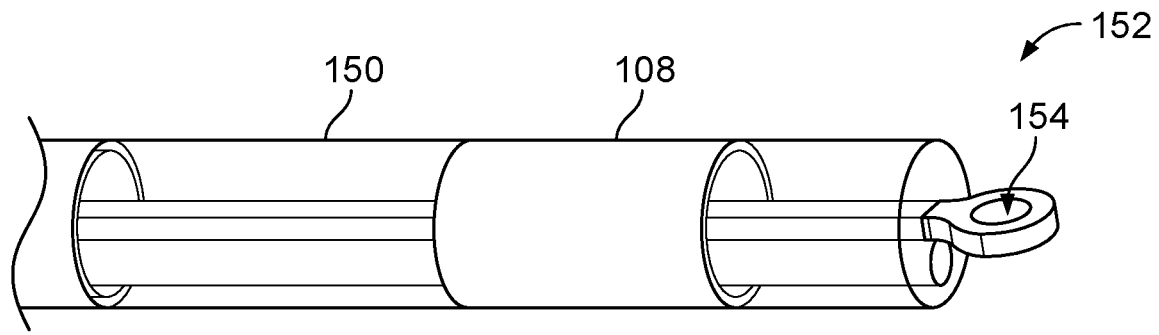
FIG. 14 is a top view of an end of a circuit board of the tissue stimulators of FIGS. 1, 11, and 12.
Figure 15:
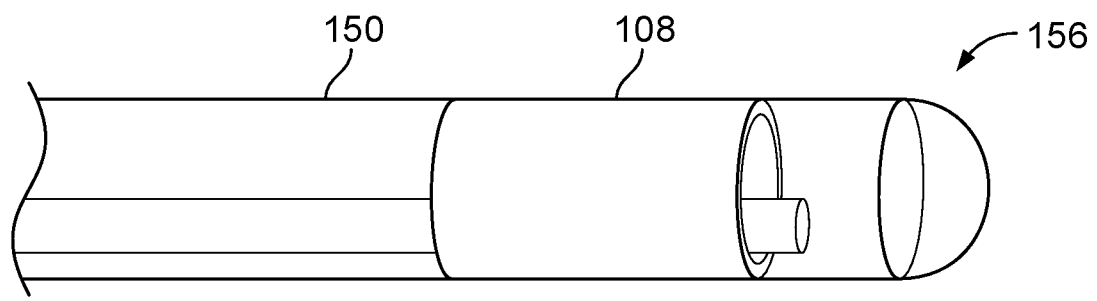
FIG. 15 is an enlarged perspective view of an end the tissue stimulators of FIGS. 1, 11, and 12 at intermediate and final manufacturing steps.

Referring to FIG. 14, either or both ends 152 of the circuit board 102 may be formed with a circular opening 154 that can be used for securing the circuit board 102 to a fixture during any of the above-discussed manufacturing processes. Referring to FIG. 15, in some embodiments, either or both ends 152 of the circuit board 102 may be clipped off and replaced with smooth, hemispherical caps 156 on the tissue stimulator 100, 300, 400.

Figure 16:
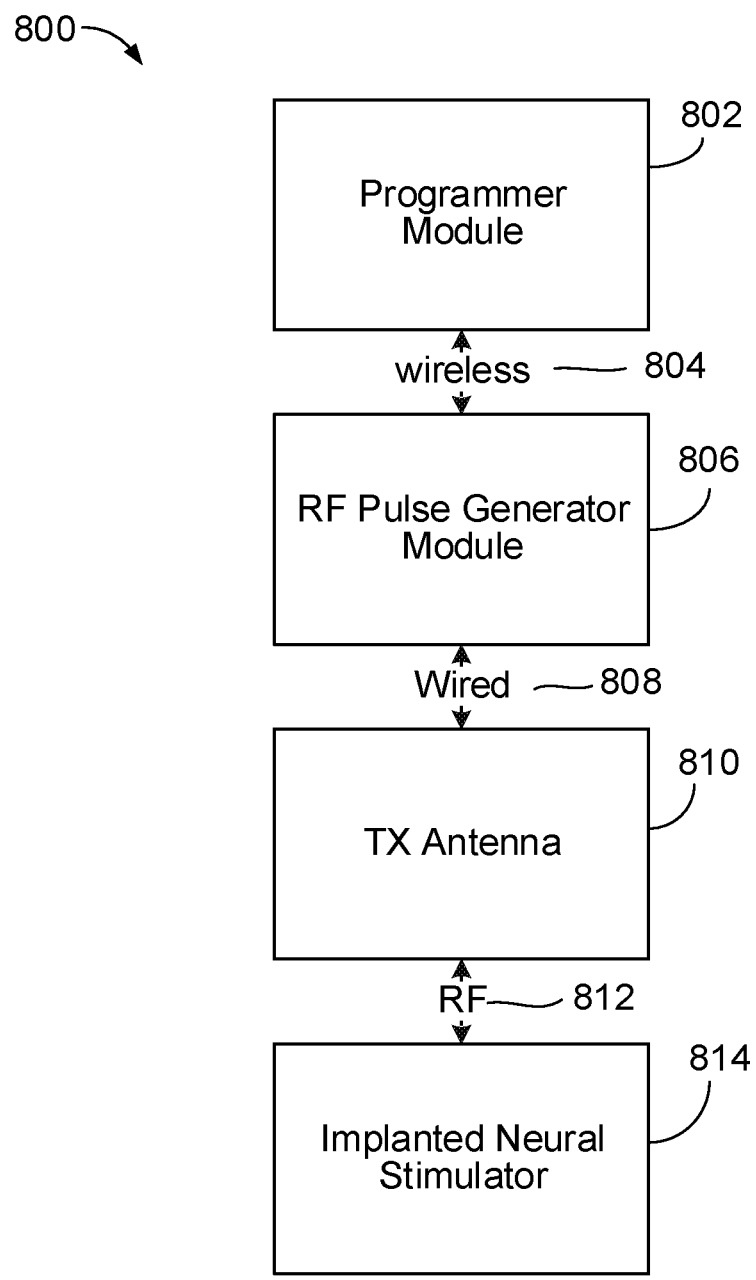
FIG. 16 is a system block diagram of the neural stimulation system of the therapy delivery system of FIG. 1.

Referring to FIG. 16, any of the tissue stimulators 100, 300, 400 may be embodied as a tissue stimulator 814 of a neural stimulation system 800. The neural stimulation system further includes a pulse generator 804 that is located exterior to the patient (e.g., handheld by the patient), a transmit (TX) antenna 810 that is connected to the pulse generator 804 and positioned against a skin surface of the patient, and a programmer module 802 that runs a software application. The neural stimulation system 800 is designed to send electrical pulses to a nearby (e.g., adjacent or surrounding) target nerve tissue to stimulate the target nerve tissue by using remote radio frequency (RF) energy without cables and without inductive coupling to power the tissue stimulator 814. Accordingly, the tissue stimulator 814 is provided as a passive tissue stimulator in the neural stimulation system 800. In some examples, the target nerve tissue is in the spinal column and may include one or more of the spinothalamic tracts, the dorsal horn, the dorsal root ganglia, the dorsal roots, the dorsal column fibers, and the peripheral nerves bundles leaving the dorsal column or the brainstem. In some examples, the target nerve tissue may include one or more of cranial nerves, abdominal nerves, thoracic nerves, trigeminal ganglia nerves, nerve bundles of the cerebral cortex, deep brain, sensory nerves, and motor nerves.

In some embodiments, the software application supports a wireless connection 804 (e.g., via Bluetooth®). The software application can enable the user to view a system status and system diagnostics, change various parameters, increase and decrease a desired stimulus amplitude of the electrical pulses, and adjust a feedback sensitivity of the RF pulse generator module 806, among other functions.

The RF pulse generator module 806 includes stimulation circuitry, a battery to power generator electronics, and communication electronics that support the wireless connection 804. In some embodiments, the RF pulse generator module 806 is designed to be worn external to the body, and the TX antenna 810 (e.g., located external to the body) is connected to the RF pulse generator module 806 by a wired connection 808. Accordingly, the RF pulse generator module 806 and the TX antenna 810 may be incorporated into a wearable accessory (e.g., a belt or a harness design) or a clothing article such that electric radiative coupling can occur through the skin and underlying tissue to transfer power and/or control parameters to the tissue stimulator 814.

The TX antenna 810 can be coupled directly to tissues within the body to create an electric field that powers the implanted tissue stimulator 814. The TX antenna 810 communicates with the tissue stimulator 814 through an RF interface. For instance, the TX antenna 810 radiates an RF transmission signal that is modulated and encoded by the RF pulse generator module 806. The tissue stimulator 814 includes one or more antennas (e.g., dipole antennas) that can receive and transmit through an RF interface 812. In particular, the coupling mechanism between the TX antenna 810 and the one or more antennas on the tissue stimulator 814 is electrical radiative coupling and not inductive coupling. In other words, the coupling is through an electric field rather than through a magnetic field. Through this electrical radiative coupling, the TX antenna 810 can provide an input signal to the tissue stimulator 814.

In addition to the one or more antennas, the tissue stimulator 814 further includes internal receiver circuit components that can capture the energy carried by the input signal sent from the TX antenna 804 and demodulate the input signal to convert the energy to an electrical waveform. The receiver circuit components can further modify the waveform to create electrical pulses suitable for stimulating the target neural tissue. The tissue stimulator 814 further includes electrodes that can deliver the electrical pulses to the target neural tissue. For example, the circuit components may include wave conditioning circuitry that rectifies the received RF signal (e.g., using a diode rectifier), transforms the RF energy to a low frequency signal suitable for the stimulation of neural tissue, and presents the resulting waveform to an array of the electrodes. In some implementations, the power level of the input signal directly determines an amplitude (e.g., a power, a current, and/or a voltage) of the electrical pulses applied to the target neural tissue by the electrodes. For example, the input signal may include information encoding stimulus waveforms to be applied at the electrodes.

In some implementations, the RF pulse generator module 806 can remotely control stimulus parameters of the electrical pulses applied to the target neural tissue by the electrodes and monitor feedback from the tissue stimulator 814 based on RF signals received from the tissue stimulator 814. For example, a feedback detection algorithm implemented by the RF pulse generator module 806 can monitor data sent wirelessly from the tissue stimulator 814, including information about the energy that the tissue stimulator 814 is receiving from the RF pulse generator 806 and information about the stimulus waveform being delivered to the electrodes. Accordingly, the circuit components internal to the tissue stimulator 814 may also include circuitry for communicating information back to the RF pulse generator module 806 to facilitate the feedback control mechanism. For example, the tissue stimulator 814 may send to the RF pulse generator module 806 a stimulus feedback signal that is indicative of parameters of the electrical pulses, and the RF pulse generator module 806 may employ the stimulus feedback signal to adjust parameters of the signal sent to the tissue stimulator 814.

In order to provide an effective therapy for a given medical condition, the neural stimulation system 800 can be tuned to provide the optimal amount of excitation or inhibition to the nerve fibers by electrical stimulation. A closed loop feedback control method can be used in which the output signals from the tissue stimulator 814 are monitored and used to determine the appropriate level of neural stimulation current for maintaining effective neuronal activation. Alternatively, in some cases, the patient can manually adjust the output signals in an open loop control method.

Figure 17:
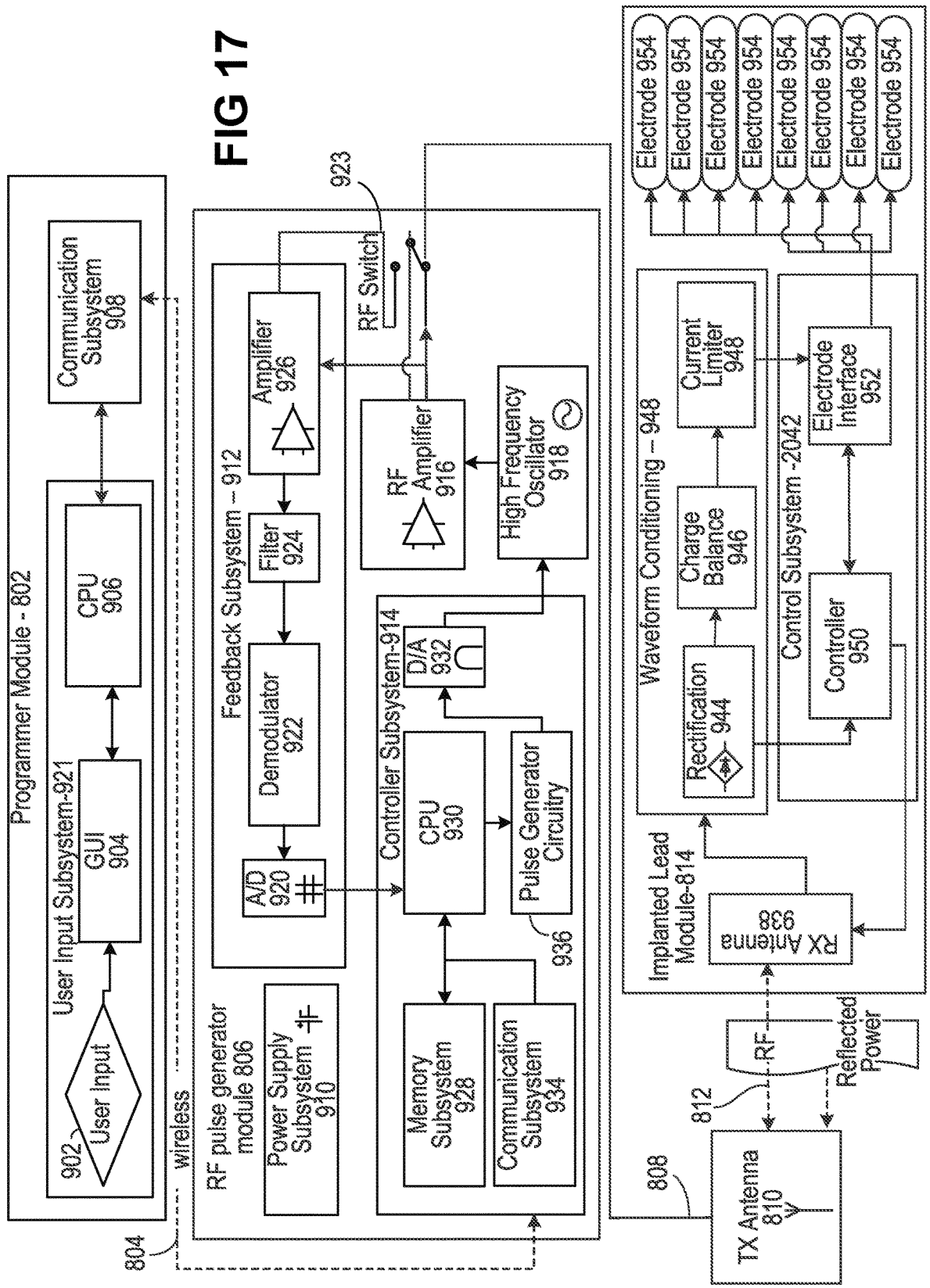
FIG. 17 is a detailed block diagram of the neural stimulation system of FIG. 16.

FIG. 17 depicts a detailed diagram of the neural stimulation system 800. The programmer module 802 may be used as a vehicle to handle touchscreen input on a graphical user interface (GUI) 904 and may include a central processing unit (CPU) 906 for processing and storing data. The programmer module 802 includes a user input system 921 and a communication subsystem 908. The user input system 921 can allow a user to input or adjust instruction sets in order to adjust various parameter settings (e.g., in some cases, in an open loop fashion). The communication subsystem 908 can transmit these instruction sets (e.g., and other information) via the wireless connection 804 (e.g., via a Bluetooth or Wi-Fi connection) to the RF pulse generator module 806. The communication subsystem 908 can also receive data from RF pulse generator module 806.

The programmer module 802 can be utilized by multiple types of users (e.g., patients and others), such that the programmer module 802 may serve as a patient's control unit or a clinician's programmer unit. The programmer module 802 can be used to send stimulation parameters to the RF pulse generator module 806. The stimulation parameters that can be controlled may include a pulse amplitude in a range of 0 mA to 20 mA, a pulse frequency in a range of 0 Hz to 2000 Hz, and a pulse width in a range of 0 ms to 2 ms. In this context, the term pulse refers to the phase of the waveform that directly produces stimulation of the tissue. Parameters of a charge-balancing phase (described below)

of the waveform can similarly be controlled. The user can also optionally control an overall duration and a pattern of a treatment.

The tissue stimulator 814 or the RF pulse generator module 806 may be initially programmed to meet specific parameter settings for each individual patient during an initial implantation procedure. Because medical conditions or the body itself can change over time, the ability to readjust the parameter settings may be beneficial to ensure ongoing efficacy of the neural modulation therapy.

Signals sent by the RF pulse generator module 806 to the tissue stimulator 814 may include both power and parameter attributes related to the stimulus waveform, amplitude, pulse width, and frequency. The RF pulse generator module 806 can also function as a wireless receiving unit that receives feedback signals from the tissue stimulator 814. To that end, the RF pulse generator module 806 includes microelectronics or other circuitry to handle the generation of the signals transmitted to the tissue stimulator 814, as well as feedback signals received from tissue stimulator 814. For example, the RF pulse generator module 806 includes a controller subsystem 914, a high-frequency oscillator 918, an RF amplifier 916, an RF switch, and a feedback subsystem 912.

The controller subsystem 914 includes a CPU 930 to handle data processing, a memory subsystem 928 (e.g., a local memory), a communication subsystem 934 to communicate with the programmer module 802 (e.g., including receiving stimulation parameters from the programmer module 802), pulse generator circuitry 936, and digital/analog (D/A) converters 932.

The controller subsystem 914 may be used by the user to control the stimulation parameter settings (e.g., by controlling the parameters of the signal sent from RF pulse generator module 806 to tissue stimulator 814). These parameter settings can affect the power, current level, or shape of the electrical pulses that will be applied by the electrodes. The programming of the stimulation parameters can be performed using the programming module 802 as described above to set a repetition rate, pulse width, amplitude, and waveform that will be transmitted by RF energy to a receive (RX) antenna 938 (e.g., or multiple RX antennas 938) within the tissue stimulator 814. The RX antenna 938 may be a dipole antenna or another type of antenna. A clinician user may have the option of locking and/or hiding certain settings within a programmer interface to limit an ability of a patient user to view or adjust certain parameters since adjustment of certain parameters may require detailed medical knowledge of neurophysiology, neuroanatomy, protocols for neural modulation, and safety limits of electrical stimulation.

The controller subsystem 914 may store received parameter settings in the local memory subsystem 928 until the parameter settings are modified by new input data received from the programmer module 802. The CPU 906 may use the parameters stored in the local memory to control the pulse generator circuitry 936 to generate a stimulus waveform that is modulated by the high frequency oscillator 918 in a range of 300 MHz to 8 GHz. The resulting RF signal may then be amplified by an RF amplifier 926 and sent through an RF switch 923 to the TX antenna 810 to reach the RX antenna 938 through a depth of tissue.

In some implementations, the RF signal sent by the TX antenna 810 may simply be a power transmission signal used by tissue stimulator 814 to generate electric pulses. In other implementations, the RF signal sent by the TX antenna 810 may be a telemetry signal that provides instructions about various operations of the tissue stimulator 814. The telemetry signal may be sent by the modulation of the carrier signal through the skin. The telemetry signal is used to modulate the carrier signal (e.g., a high frequency signal) that is coupled to the antenna 938 and does not interfere with the input received on the same lead to power the tissue stimulator 814. In some embodiments, the telemetry signal and the powering signal are combined into one signal, where the RF telemetry signal is used to modulate the RF powering signal such that the tissue stimulator 814 is powered directly by the received telemetry signal. Separate subsystems in the tissue stimulator 814 harness the power contained in the signal and interpret the data content of the signal.

The RF switch 923 may be a multipurpose device (e.g., a dual directional coupler) that passes the relatively high amplitude, extremely short duration RF pulse to the TX antenna 810 with minimal insertion loss, while simultaneously providing two low-level outputs to the feedback subsystem 912. One output delivers a forward power signal to the feedback subsystem 912, where the forward power signal is an attenuated version of the RF pulse sent to the TX antenna 810, and the other output delivers a reverse power signal to a different port of the feedback subsystem 912, where reverse power is an attenuated version of the reflected RF energy from the TX Antenna 810.

During the on-cycle time (e.g., while an RF signal is being transmitted to tissue stimulator 814), the RF switch 923 is set to send the forward power signal to feedback subsystem 912. During the off-cycle time (e.g., while an RF signal is not being transmitted to the tissue stimulator 814), the RF switch 923 can change to a receiving mode in which the reflected RF energy and/or RF signals from the tissue stimulator 814 are received to be analyzed in the feedback subsystem 912.

The feedback subsystem 912 of the RF pulse generator module 806 may include reception circuitry to receive and extract telemetry or other feedback signals from tissue stimulator 814 and/or reflected RF energy from the signal sent by TX antenna 810. The feedback subsystem 912 may include an amplifier 926, a filter 924, a demodulator 922, and an A/D converter 920. The feedback subsystem 912 receives the forward power signal and converts this high-frequency AC signal to a DC level that can be sampled and sent to the controller subsystem 914. In this way, the characteristics of the generated RF pulse can be compared to a reference signal within the controller subsystem 914. If a disparity (e.g., an error) exists in any parameter, the controller subsystem 914 can adjust the output to the RF pulse generator 806. The nature of the adjustment can be proportional to the computed error. The controller subsystem 914 can incorporate additional inputs and limits on its adjustment scheme, such as the signal amplitude of the reverse power and any predetermined maximum or minimum values for various pulse parameters.

The reverse power signal can be used to detect fault conditions in the RF-power delivery system. In an ideal condition, when TX antenna 810 has perfectly matched impedance to the tissue that it contacts, the electromagnetic waves generated from the RF pulse generator module 806 pass unimpeded from the TX antenna 810 into the body tissue. However, in real-world applications, a large degree of variability exists in the body types of users, types of clothing worn, and positioning of the antenna 810 relative to the body surface. Since the impedance of the antenna 810 depends on the relative permittivity of the underlying tissue and any intervening materials and on an overall separation distance of the antenna 810 from the skin, there can be an impedance mismatch at the interface of the TX antenna 810 with the body surface in any given application. When such a mismatch occurs, the electromagnetic waves sent from the RF pulse generator module 806 are partially reflected at this interface, and this reflected energy propagates backward through the antenna feed.

The dual directional coupler RF switch 923 may prevent the reflected RF energy propagating back into the amplifier 926, and may attenuate this reflected RF signal and send the attenuated signal as the reverse power signal to the feedback subsystem 912. The feedback subsystem 912 can convert this high-frequency AC signal to a DC level that can be sampled and sent to the controller subsystem 914. The controller subsystem 914 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 914 can measure the reflected-power ratio in real time, and according to preset thresholds for this measurement, the controller subsystem 914 can modify the level of RF power generated by the RF pulse generator module 806. For example, for a moderate degree of reflected power the course of action can be for the controller subsystem 914 to increase the amplitude of RF power sent to the TX antenna 810, as would be needed to compensate for slightly non-optimum but acceptable TX antenna coupling to the body. For higher ratios of reflected power, the course of action can be to prevent operation of the RF pulse generator module 806 and set a fault code to indicate that the TX antenna 810 has little or no coupling with the body. This type of reflected power fault condition can also be generated by a poor or broken connection to the TX antenna 810. In either case, it may be desirable to stop RF transmission when the reflected power ratio is above a defined threshold, because internally reflected power can lead to unwanted heating of internal components, and this fault condition means that the system cannot deliver sufficient power to the tissue stimulator 814 and thus cannot deliver therapy to the user.

The controller 942 of the tissue stimulator 814 may transmit informational signals, such as a telemetry signal, through the RX antenna 538 to communicate with the RF pulse generator module 806 during its receive cycle. For example, the telemetry signal from the tissue stimulator 814 may be coupled to the modulated signal on the RX antenna 938, during the on and off state of the transistor circuit to enable or disable a waveform that produces the corresponding RF bursts necessary to transmit to the external (or remotely implanted) pulse generator module 806. The RX antenna 938 may be connected to electrodes 954 in contact with tissue to provide a return path for the transmitted signal. An A/D converter can be used to transfer stored data to a serialized pattern that can be transmitted on the pulse modulated signal from the RX antenna 938 of the tissue stimulator 814.

A telemetry signal from the tissue stimulator 814 may include stimulus parameters, such as the power or the amplitude of the current that is delivered to the tissue from the electrodes 954. The feedback signal can be transmitted to the RF pulse generator module 806 to indicate the strength of the stimulus at the target nerve tissue by means of coupling the signal to the RX antenna 938, which radiates the telemetry signal to the RF pulse generator module 806. The feedback signal can include either or both an analog and digital telemetry pulse modulated carrier signal. Data such as stimulation pulse parameters and measured characteristics of stimulator performance can be stored in an internal memory device within the tissue stimulator 814 and sent on the telemetry signal. The frequency of the carrier signal may be in a range of 300 MHz to 8 GHz.

In the feedback subsystem 912, the telemetry signal can be down modulated using the demodulator 922 and digitized by being processed through the analog to digital (A/D) converter 920. The digital telemetry signal may then be routed to the CPU 930 with embedded code, with the option to reprogram, to translate the signal into a corresponding current measurement in the tissue based on the amplitude of the received signal. The CPU 930 of the controller subsystem 914 can compare the reported stimulus parameters to those held in local memory 928 to verify that the tissue stimulator 814 delivered the specified stimuli to target nerve tissue. For example, if the tissue stimulator 814 reports a lower current than was specified, the power level from the RF pulse generator module 806 can be increased so that the tissue stimulator 814 will have more available power for stimulation. The tissue stimulator 814 can generate telemetry data in real time (e.g., at a rate of 8 kbits per second). All feedback data received from the tissue stimulator 814 can be logged against time and sampled to be stored for retrieval to a remote monitoring system accessible by a health care professional for trending and statistical correlations.

The sequence of remotely programmable RF signals received by the RX antenna 938 may be conditioned into waveforms that are controlled within the tissue stimulator 814 by the control subsystem 942 and routed to the appropriate electrodes 954 that are located in proximity to the target nerve tissue. For instance, the RF signal transmitted from the RF pulse generator module 806 may be received by RX antenna 938 and processed by circuitry, such as waveform conditioning circuitry 940, within the tissue stimulator 814 to be converted into electrical pulses applied to the electrodes 954 through an electrode interface 952. In some implementations, the tissue stimulator 814 includes between two to sixteen electrodes 954.

The waveform conditioning circuitry 940 may include a rectifier 944, which rectifies the signal received by the RX antenna 938. The rectified signal may be fed to the controller 942 for receiving encoded instructions from the RF pulse generator module 806. The rectifier signal may also be fed to a charge balance component 946 that is configured to create one or more electrical pulses such that the one or more electrical pulses result in a substantially zero net charge at the one or more electrodes 954 (that is, the pulses are charge balanced). The charge balanced pulses are passed through the current limiter 948 to the electrode interface 952, which applies the pulses to the electrodes 954 as appropriate.

The current limiter 948 insures the current level of the pulses applied to the electrodes 954 is not above a threshold current level. In some implementations, an amplitude (for example, a current level, a voltage level, or a power level) of the received RF pulse directly determines the amplitude of the stimulus. In this case, it may be particularly beneficial to include current limiter 948 to prevent excessive current or charge being delivered through the electrodes 954, although the current limiter 548 may be used in other implementations where this is not the case. Generally, for a given electrode 954 having several square millimeters of surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the current limiter 948 acts as a charge limiter that limits a characteristic (for example, a current or duration) of the electrical pulses so that the charge per phase remains below a threshold level (typically, a safe-charge limit).

In the event the tissue stimulator 814 receives a "strong" pulse of RF power sufficient to generate a stimulus that would exceed the predetermined safe-charge limit, the current limiter 948 can automatically limit or "clip" the stimulus phase to maintain the total charge of the phase within the safety limit. The current limiter 948 may be a passive current limiting component that cuts the signal to the electrodes 954 once the safe current limit (the threshold current level) is reached. Alternatively, or additionally, the current limiter 948 may communicate with the electrode interface 952 to turn off all electrodes 954 to prevent tissue damaging current levels.

A clipping event may trigger a current limiter feedback control mode. The action of clipping may cause the controller to send a threshold power data signal to the RF pulse generator module 806. The feedback subsystem 912 detects the threshold power signal and demodulates the signal into data that is communicated to the controller subsystem 914. The controller subsystem 914 algorithms may act on this current-limiting condition by specifically reducing the RF power generated by the RF pulse generator module 806, or cutting the power completely. In this way, the RF pulse generator module 806 can reduce the RF power delivered to the body if the tissue stimulator 814 reports that it is receiving excess RF power.

The controller 950 may communicate with the electrode interface 952 to control various aspects of the electrode setup and pulses applied to the electrodes 954. The electrode interface 952 may act as a multiplex and control the polarity and switching of each of the electrodes 954. For instance, in some implementations, the tissue stimulator 814 has multiple electrodes 954 in contact with the target neural tissue, and for a given stimulus, the RF pulse generator module 806 can arbitrarily assign one or more electrodes to act as a stimulating electrode, to act as a return electrode, or to be inactive by communication of assignment sent wirelessly with the parameter instructions, which the controller 950 uses to set electrode interface 952 as appropriate. It may be physiologically advantageous to assign, for example, one or two electrodes 954 as stimulating electrodes and to assign all remaining electrodes 954 as return electrodes.

Also, in some implementations, for a given stimulus pulse, the controller 950 may control the electrode interface 952 to divide the current arbitrarily (or according to instructions from the RF pulse generator module 806) among the designated stimulating electrodes. This control over electrode assignment and current control can be advantageous because in practice the electrodes 954 may be spatially distributed along various neural structures, and through strategic selection of the stimulating electrode location and the proportion of current specified for each location, the aggregate current distribution on the target neural tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T final, and this time course may be synchronized across all stimulating and return electrodes. Furthermore, the frequency of repetition of this stimulus cycle may be synchronous for all of the electrodes 954. However, the controller 950, on its own or in response to instructions from the RF pulse generator module 806, can control electrode interface 952 to designate one or more subsets of electrodes to deliver stimulus waveforms with non-synchronous start and stop times, and the frequency of repetition of each stimulus cycle can be arbitrarily and independently specified.

For example, a tissue stimulator 814 having eight electrodes 954 may be configured to have a subset of five electrodes, called set A, and a subset of three electrodes, called set B. Set A may be configured to use two of its electrodes as stimulating electrodes, with the remainder being return electrodes. Set B may be configured to have just one stimulating electrode. The controller 950 could then specify that set A deliver a stimulus phase with 3 mA current for a duration of 200 us, followed by a 400 us charge-balancing phase. This stimulus cycle could be specified to repeat at a rate of 60 cycles per second. Then, for set B, the controller 950 could specify a stimulus phase with 1 mA current for duration of 500 us, followed by a 800 us charge-balancing phase. The repetition rate for the set B stimulus cycle can be set independently of set A (e.g., at 25 cycles per second). Or, if the controller 950 was configured to match the repetition rate for set B to that of set A, for such a case the controller 950 can specify the relative start times of the stimulus cycles to be coincident in time or to be arbitrarily offset from one another by some delay interval.

In some implementations, the controller 950 can arbitrarily shape the stimulus waveform amplitude, and may do so in response to instructions from the RF pulse generator module 806. The stimulus phase may be delivered by a constant-current source or a constant-voltage source, and this type of control may generate characteristic waveforms that are static. For example, a constant current source generates a characteristic rectangular pulse in which the current waveform has a very steep rise, a constant amplitude for the duration of the stimulus, and then a very steep return to baseline. Alternatively, or additionally, the controller 950 can increase or decrease the level of current at any time during the stimulus phase and/or during the charge-balancing phase. Thus, in some implementations, the controller 950 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the tissue stimulator 814 may include a charge balancing component 946. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units $uC/cm^2$. In order to avoid the irreversible electrochemical reactions such as pH change, electrode dissolution as well as tissue destruction, no net charge should appear at the electrode-electrolyte interface, and it is generally acceptable to have a charge density less than 30 $uC/cm^2$. Biphasic stimulating current pulses ensure that no net charge appears at the electrode 954 after each stimulation cycle and that the electrochemical processes are balanced to prevent net dc currents. The tissue stimulator 814 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode 954 that delivers a negative current with sufficient amplitude to stimulate adjacent neural tissue is called a "stimulating electrode." During the stimulus phase, the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 946 uses one or more blocking capacitors placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitors may be used for each electrode, or a centralized capacitors may be used within the stimulator circuitry prior to the point of electrode selection. The RC network can block direct current (DC). However, the RC network can also prevent low-frequency alternating current (AC) from passing to the tissue. The frequency below which the series RC network essentially blocks signals is commonly referred to as the cutoff frequency, and in some embodiments, the design of the stimulator system may ensure that the cutoff frequency is not above the fundamental frequency of the stimulus waveform. In the example embodiment 800, the tissue stimulator 814 may have a charge-balance capacitor with a value chosen according to the measured series resistance of the electrodes and the tissue environment in which the stimulator is implanted. By selecting a specific capacitance value, the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the tissue stimulator 814 may create a drive-waveform envelope that follows the envelope of the RF pulse received by the RX antenna 938. In this case, the RF pulse generator module 806 can directly control the envelope of the drive waveform within the tissue stimulator 814, and thus no energy storage may be required inside of the tissue stimulator 814, itself. In this implementation, the stimulator circuitry may modify the envelope of the drive waveform or may pass it directly to the charge-balance capacitor and/or electrode-selection stage.

In some implementations, the tissue stimulator 814 may deliver a single-phase drive waveform to the charge balance capacitor or it may deliver multiphase drive waveforms. In the case of a single-phase drive waveform (e.g., a negative-going rectangular pulse), this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the tissue stimulator 814 facilitates the discharge of the charge-balance capacitor. In some implementations, using a passive discharge phase, the capacitor may allow virtually complete discharge prior to the onset of the subsequent stimulus pulse.

In the case of multiphase drive waveforms, the tissue stimulator 814 may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 806, and in other implementations, this control may be administered internally by circuitry onboard the tissue stimulator 814, such as controller 550. In the case of onboard control, the amplitude and timing may be specified or modified by data commands delivered from the pulse generator module 806.

While the RF pulse generator module 806 and the TX antenna 810 have been described and illustrated as separate components, in some embodiments, the RF pulse generator module 806 and the TX antenna 810 may be physically located in the same housing or other packaging. Furthermore, while the RF pulse generator module 806 and the TX antenna 810 have been described and illustrated as located external to the body, in some embodiments, either or both of the RF pulse generator module 806 and the TX antenna 810 may be designed to be implanted subcutaneously. While the RF pulse generator module 806 and the TX antenna 810 have been described and illustrated as coupled via a wired connection 808, in some embodiments (e.g., where the RF pulse generator module 806 is either located externally or implanted subcutaneously), the RF pulse generator module 806 and the TX antenna 810 may be coupled via a wireless connection.

Other embodiments of tissue stimulation systems, tissue stimulators, leads, and methods of manufacturing tissue stimulators and leads are within the scope of the following claims. For example, the improved techniques described above with respect to manufacturing the tissue stimulators 100, 300, 400 can also provide an improved lead, where a substantially simplified circuit board replaces the above-described stimulator circuit board, circuit components, and antenna. In an embodiment of such an improved lead, the circuit board acts as the electrical conduit, replacing standard cables (e.g., wires) that are commonly attached to electrodes. This alternative design results in a substantially stronger lead that is more easily assembled, more flexible, that can withstand more bending forces, that is more mechanically robust within a moving body, and that allows for more uniform assembly of electrodes, as discussed above with respect to the tissue stimulators 100, 300, 400.

What is claimed is:

1. A method of manufacturing an implantable stimulation device, the method comprising:
   providing a circuit board of the implantable stimulation device, the circuit board being equipped with circuit components and being electrically connected to an antenna;
   attaching one or more joints to the circuit board;
   after attaching the one or more joints, adhering one or more electrodes to the circuit board respectively by the one or more joints such that the electrodes are directly coupled to the circuit board by the one or more joints; and
   applying an insulation material to the circuit board such that the insulation material forms a housing that surrounds the circuit board, the circuit components, and the antenna, while leaving the one or more electrodes exposed for stimulating a tissue.

2. The method of claim 1, further comprising attaching the one or more joints to the circuit board automatically by soldering, laser welding, or applying a conductive epoxy.

3. The method of claim 1, further comprising forming the one or more joints such that each of the one or more joints has a cube-like shape.

4. The method of claim 1, further comprising placing an assembly of the circuit board, equipped with the circuit components, the antenna, and the one or more electrodes, within an injection mold and filling the injection mold with the insulation material to form the housing of the implantable stimulation device.

5. The method of claim 1, wherein the insulation material comprises silicone rubber.

6. The method of claim 1, further comprising dip coating an assembly of the circuit board, equipped with the circuit components, the antenna, and the one or more electrodes, to form the housing of the implantable stimulation device.

7. A method of manufacturing an implantable stimulation device, the method comprising:
   providing a circuit board of the implantable stimulation device, the circuit board being equipped with circuit components and being electrically connected to an antenna;
   positioning at least a portion of the circuit board atop a support component, the support component defining a through opening sized to allow passage of a surgical tool;
   covering at least a portion of the circuit board with a protective component, the protective component defining a channel that accommodates the circuit components on the circuit board;
   adhering one or more electrodes to the circuit board; and
   applying an insulation material to the circuit board such that the insulation material forms a housing that surrounds the circuit board, the circuit components, and the antenna, while leaving the one or more electrodes exposed for stimulating a tissue.

8. The method of claim 7, further comprising:
   alternately placing one or more spacers and the one or more electrodes over an assembly of the support component and the circuit board; and
   adhering the one or more spacers and the one or more electrodes to the circuit board.

9. The method of claim 8, wherein the one or more spacers comprise carbothane.

10. The method of claim 9, wherein the assembly is a first assembly, wherein the first assembly, the one or more spacers, the one or more electrodes, and an extended housing component together form a second assembly, and wherein the method further comprises automatically surrounding the second assembly with a heat shrink tube.

11. The method of claim 10, wherein at least a portion of the insulation material of the implantable stimulation device is provided by at least one of the extended housing component and the one or more spacers.

12. The method of claim 10, further comprising:
   securing the second assembly, equipped with the heat shrink tube, to a clamp of a reflow tower; and
   translating a heating element shuttle of the reflow tower along the second assembly to flow the insulation material around the second assembly.

13. A method of manufacturing an implantable stimulation device, the method comprising:
   providing a circuit board of the implantable stimulation device, the circuit board being equipped with circuit components and being electrically connected to an antenna;
   placing a conductive material on the circuit board at a location;
   after placing the conductive material, moving one or more of the circuit board and an electrode such that a portion of the circuit board passes through an opening of the electrode to position the conductive material in the opening of the electrode; and
   attaching the electrode to the circuit board at the location using the conductive material.

14. The method of claim 13, further comprising after attaching the electrode to the circuit board, applying an insulation material to the circuit board such that the insulation material forms a housing that surrounds the circuit board, the circuit components, and the antenna, while leaving the electrode exposed for stimulating a tissue.

15. The method of claim 13, further comprising moving one or more of the circuit board and a spacer such that the portion of the circuit board passes through an opening of the spacer to position the spacer along the circuit board.

16. The method of claim 13, further comprising before moving one or more of the circuit board and the electrode, positioning at least the portion of the circuit board atop a support component, the support component defining a through opening sized to allow passage of a surgical tool, wherein the support component slides through the opening of the electrode with the portion of the circuit board.

17. The method of claim 13, wherein the circuit board has a length that extends from a first end of the implantable stimulation device to a second end of the implantable stimulation device, the length of the circuit board is coupled to the circuit components and the electrode, and the length of the circuit board is planar.

18. The method of claim 17, wherein the conductive material has a cross-sectional shape that is triangular, square, circular, square-round, or rectangular.

* * * * *